(12) United States Patent
Lei et al.

(10) Patent No.: US 7,691,984 B2
(45) Date of Patent: Apr. 6, 2010

(54) METAL COMPLEXES OF TRIDENTATE β-KETOIMINATES

(75) Inventors: Xinjian Lei, Vista, CA (US); Daniel P. Spence, San Diego, CA (US); Hansong Cheng, Allentown, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 245 days.

(21) Appl. No.: 11/945,678

(22) Filed: Nov. 27, 2007

(65) Prior Publication Data

US 2009/0136677 A1    May 28, 2009

(51) Int. Cl.
C23C 16/22    (2006.01)
C07F 5/00    (2006.01)
C07F 9/00    (2006.01)
C07F 13/00    (2006.01)

(52) U.S. Cl. .................. 534/15; 556/42; 556/45; 556/113; 556/137; 556/146; 427/255.395; 427/453

(58) Field of Classification Search .................. 534/15; 427/255.395, 453; 556/113, 146, 42, 45, 556/137
See application file for complete search history.

(56) References Cited

U.S. PATENT DOCUMENTS 5,820,664 A    10/1998  Gardiner et al.
2007/0248754 A1*  10/2007  Lei et al. .................. 427/248.1

FOREIGN PATENT DOCUMENTS

| EP | 369297 B1 | 8/1993 |
| EP | 1227079 A2 | 7/2002 |
| EP | 1 273 683 A2 | 1/2003 |
| EP | 1 676 849 A | 7/2006 |
| EP | 1 676 850 A | 7/2006 |
| EP | 1 676 850 A1 | 7/2006 |

(Continued)

OTHER PUBLICATIONS

Douglas L Schulz, et al, New Precursors for Barium MOCVD, Inorg. Chem., 1993, 249-250, 32, 3, Amer. Chem. Soc.

(Continued)

*Primary Examiner*—Porfirio Nazario Gonzalez
(74) *Attorney, Agent, or Firm*—Lina Yang

(57) ABSTRACT

Metal-containing complexes of a tridentate beta-ketoiminate, one embodiment of which is represented by the structure:

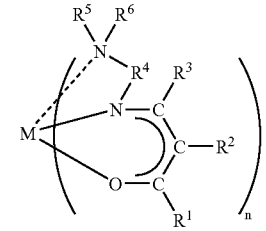

wherein M is a metal such as calcium, strontium, barium, scandium, yttrium, lanthanum, titanium, zirconium, vanadium, tungsten, manganese, cobalt, iron, nickel, ruthenium, zinc, copper, palladium, platinum, iridium, rhenium, osmium; $R^1$ is selected from the group consisting of alkyl, fluoroalkyl, cycloaliphatic, and aryl, having 1 to 10 carbon atoms; $R^2$ is selected from the group consisting of hydrogen, alkyl, alkoxy, cycloaliphatic, and aryl; $R^3$ is linear or branched selected from the group consisting of alkylene, fluoroalkyl, cycloaliphatic, and aryl; $R^4$ is a branched alkylene bridge with at least one chiral center; $R^{5-6}$ are individually linear or branched selected from the group consisting of alkyl, fluoroalkyl, cycloaliphatic, aryl, and can be connected to form a ring containing carbon, oxygen, or nitrogen atoms; n is an integer equal to the valence of the metal M.

21 Claims, 5 Drawing Sheets

FOREIGN PATENT DOCUMENTS

| | | |
|---|---|---|
| EP | 1 849 789 A1 | 10/2007 |
| JP | 6-298714 A | 10/1994 |
| JP | 2002-193988 A | 7/2002 |
| WO | 02/18394 A1 | 3/2002 |
| WO | 2004002946 A1 | 1/2004 |

OTHER PUBLICATIONS

Sergej Pasko, et al, Synthesis and Characterization of New Alkaline Earth Metal B-ketoiminates. Inorg. Chem., 2005, 483-487, 8, Elsevier B.V.

Pier Luigi Franceschini, et al, Volatile B-Ketoiminato- and B-Diketiminator-Based Zirconium Complexes as Potential MOCVD Precursors, Inorg. Chem., 2003, 7273-7282, 42, Amer. Chem. Soc.

Tsung-Yi Chou, et al, Synthesis and Characterization of Tris (B-ketoiminator) ruthenium(III) Complexes: . . . Chem. Vap. Deposition, 2004, 10, 3, 149-158.

Sunkwon Lim, et al, A Study on the Development of Chemical Vapor Deposition Precursors. 4. Synthesis and . . . Chem. Mater., 2002, 14, 1548-1554, Amer. Chem. Soc.

Sunkwon Lim, et al, A Study on the Development of CVD Precursors V—synthesis and Characterization of new N-alkoxy-B-ketoiminate Comlexes of Titanium, Jour. Organ. Chem., 2004, 689, 224-237, Elsevier B.V.

Nikki L. Edleman, et al, Synthesis and Characterization of Volatile, Fluorine-Free B-Ketoiminate Lanthanide MOCVD Precursors and Their Implementation In . . . Inorg. Chem., 2002, 41, 5005-5023, Amer. Chem. Soc.

Daniel B. Studebaker, et al, Encapsulating Bis(B-Ketoiminator) Polyethers, Volatile, Fluorine-Free Barium Precursors for Metal . . . Inorg. Chem., 2000, 39, 3148-3157, Amer. Chem. Soc.

Jason S. Matthews, et al, Group 2 Element Precursors for the Chemical Vapor Deposition of Electronic Materials, Adv. in Inorg. Chem., 50, 2000, 173-192, Academic Press.

Loeb, S.J., et al; "Coordination Modes of Polydentate Ligands. 2. Template Synthesis of Four-, Five-, and Six-Coordinate Fluorinated Schiff-Base Complexes of Ni2+: Structure of an Octahedral Ni2+ Complex Containing Two Tridentate Ligands"; Inorganic Chemistry; vol. 23; 1984; pp. 1509-1512.

Becht, M., et al; "117. Synthesis Crystal Structure, and Thermal Behaviour of Some New Cooper Complexes with Tridentate β-Iminoketone Ligands"; Helvetica Chimica Acta; 1994; vol. 77(5); pp. 1288-1298.

Edwards D.A., et al; "Aerosol-Assisted Chemical Vapour Deposition (AACVD) of Silver Films from Triphyenylphospine Adducts of Silver .Beta.-diketonates and .Beta.-diketoiminates, Including the Structure of [Ag(hfac)(PPh3)]"; Journal of Materials Chemistry; vol. 9, No. 8; 1999; pp. 1771-1780; XP002372344.

Bouquillon S, et al; "Simultaneous Generation of Anionic and Neutral Palladium(II) Complexes from Eta3-Allylpalladium Chloride Dimer and Fluorinated Beta-Enaminones"; European Journal of Organic Chemistry; No. 24; 2003; pp. 4714-4720; XP002372342.

Tung Y-L, et al; "Synthesis and Characterization of Allyl(Beta-Ketoiminato)Palladium (II) Complexes: New Precursors for Chemical Vapor Deposition of Palladium Thin Films"; Organometallics; vol. 18, No. 5; Feb. 5, 1999; pp. 864-869; XP002372343.

Collier W, et al; "Kinetics of Acid Hydrolysis of Nickel(II) and Copper(II) Compounds with the Cyclic Diamines 1,5-Diazocane, and 4,4-Dimethyl-7-(5,5,7-Trim Ethyl-1,4-Diazepan-1-Yl)-5-Azaheptan-2-Ol"; Australian Journal of Chemistry; vol. 42, No. 9; 1989; pp. 1611-1616; XP009089097.

Konefal E, et al; "Coordination Modes of Polydentate Ligands. 1. Template Synthesis of Complexes of Nickel(2+), Copper(2+), and Cobalt(2+) with Pentadentate and Hexadentate Ligands: Structure of a Highly Distorted Six-Coordinate Cobalt(2+) Complex"; Inorganic Chemistry; vol. 23, No. 5; 1984; pp. 538-545; XP009079427.

Curtis N.F., et al; "Preparations, Magnetic Susceptibility and Structural Studies of Trinuclear Copper(II) Compounds of 4,4,9,9-Tetramethyl-5,8-Diazadodecane-2,11-Diol"; Australian Journal of Chemistry; vol. 41, No. 10; 1988; pp. 1545-1555; XP009089095.

Morgan, K.R., et al; "Preparation, and Complexes with Nickel(II) and Copper(II), of a Diazepane Amine Alcohol. The Structure of [4,4-Dimethyl-7-(5,5,7-Trimethyl-1,4-Diazepan-1-Yl)-5-Azaheptan-2-Ol]Nickel (II) Perchlorate"; Austrailian Journal of Chemistry; vol. 36, No. 7; 1983; pp. 1341-1351; XP009089096.

Martin J.W.L., et al; "Fluorinated Alkoxides. Part XIII. The Reduction of Beta-Imino-Alkoxy Complexes to give Stable, Polydentate, Amino Alcohols"; Canadian Journal of Chemistry; vol. 56, No. 23; 1978; pp. 2966-2969; XP009089101.

* cited by examiner

METAL COMPLEXES OF TRIDENTATE β-KETOIMINATES

BACKGROUND OF THE INVENTION

The semiconductor fabrication industry continues to demand novel metal source containing precursors for chemical vapor deposition processes including atomic layer deposition for fabricating conformal metal containing films on substrates such as silicon, metal nitride, metal oxide and other metal-containing layers using these metal-containing precursors.

BRIEF SUMMARY OF THE INVENTION

This invention is directed to metal containing tridentate β-ketoiminates and solutions wherein the tridentate β-ketoiminates incorporate nitrogen or oxygen functionality in the imino group. The tridentate β-ketoiminates are selected from the group represented by the structures:

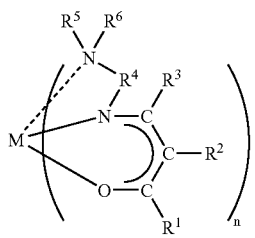

A wherein M is a metal having a valence of from 2 to 5. Examples of metals include calcium, magnesium, strontium, barium, scandium, yttrium, lanthanum, titanium, zirconium, vanadium, tungsten, manganese, cobalt, iron, nickel, ruthenium, zinc, copper, palladium, platinum, iridium, rhenium, and osmium. A variety of organo groups may be employed as for example wherein $R^1$ is selected from the group consisting of alkyl, fluoroalkyl, cycloaliphatic, and aryl, having from 1 to 10 carbon atoms, preferably a group containing 1 to 6 carbon atoms; $R^2$ is selected from the group consisting of hydrogen, alkyl, alkoxy, cycloaliphatic, and aryl; $R^3$ is selected from the group consisting of alkyl, fluoroalkyl, cycloaliphatic, and aryl; $R^4$ is a $C_{3-10}$ branched alkylene bridge having at least one chiral carbon atom, preferably a group containing 3 or 4 carbon atoms, thus making a five- or six-membered coordinating ring to the metal center; $R^{5-6}$ are individually selected from the group consisting of alkyl, fluoroalkyl, cycloaliphatic, aryl, and they can be connected to form a ring containing carbon, oxygen, or nitrogen atoms. The subscript n is an integer and equals the valence of the metal M.

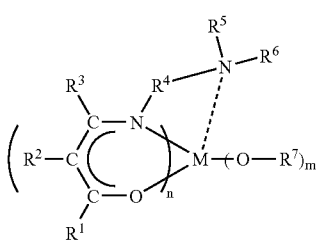

B wherein M is a metal ion selected from Group 4, 5 metals including titanium, zirconium, and hafnium; wherein $R^1$ is selected from the group consisting of alkyl, fluoroalkyl, cycloaliphatic, and aryl, preferably a group containing 1 to 6 carbon atoms; $R^2$ is selected from the group consisting of hydrogen, alkyl, alkoxy, cycloaliphatic, and aryl; $R^3$ is selected from the group consisting of alkyl, fluoroalkyl, cycloaliphatic, and aryl; $R^4$ is a $C_{3-10}$ branched alkylene bridge having at least one chiral carbon atom, preferably a group containing 3 or 4 carbon atoms, thus making a five- or six-membered coordinating ring to the metal center; $R^{5-6}$ are individually selected from the group consisting of alkyl, fluoroalkyl, cycloaliphatic, aryl, and they can be connected to form a ring containing carbon, oxygen, or nitrogen atoms; $R^7$ is selected from the group consisting of alkyl, fluoroalkyl, cycloaliphatic, and aryl; wherein m and n are at least 1 and the sum of m+n is equal to the valence of the metal.

Several advantages can be achieved through these metal-containing tridentate β-ketoiminates as precursors for chemical vapor deposition or atomic layer deposition, and these include:

- an ability to form reactive complexes in good yield;
- an ability to form monomeric complexes, particularly calcium and strontium complexes, coordinated with one kind of ligand, thus allowing one to achieve a high vapor pressure;
- an ability to significantly increase the thermal stability of resulting metal complexes via introduction of branched alkylene bridge having at least one chiral carbon atom between the two nitrogen atoms compared to those without chiral centers between the two nitrogen atoms
- an ability to produce highly conformal metal thin films suited for use in a wide variety of electrical applications;
- an ability to form highly conformal metal oxide thin films suited for use in microelectronic devices;
- an ability to enhance the surface reaction between the metal-containing tridentate β-ketoiminates and the surface of a substrate due to the high chemical reactivity of the complexes.

DETAILED DESCRIPTION OF THE INVENTION

Figure 1:
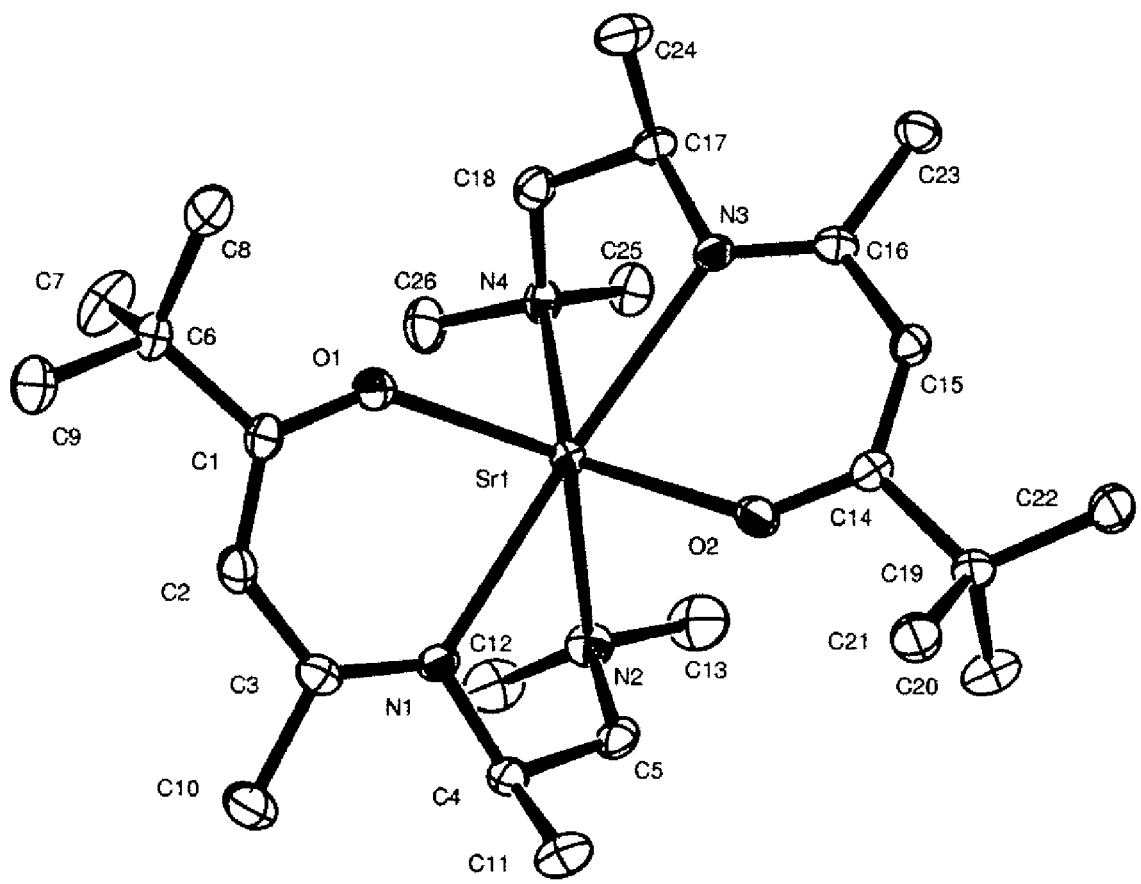
FIG. 1 is a drawing representative of the crystal structure of bis(2,2-dimethyl-5-(1-dimethylamino-2-propylimino)-3-hexanonato-N,O,N')strontium.

This invention is related to metal-containing tridentate β-ketoiminate precursors and their solutions which are useful for fabricating conformal metal containing films on substrates such as silicon, metal nitride, metal oxide and other metal layers via deposition processes, e.g., CVD and ALD. Such conformal metal containing films have applications ranging from computer chips, optical device, magnetic information storage, to metallic catalyst coated on a supporting material. In contrast to prior tridentate β-ketoiminate precursors, the tridentate β-ketoiminate ligands incorporate at least one amino organo imino functionality which is in contrast to the literatures reported alkoxy group as the donating ligand, most importantly they contain a branched alkylene bridge having at least one chiral carbon atom between the two nitrogen atoms.

Oxidizing agents for vapor deposition process include oxygen, hydrogen peroxide and ozone and reducing agents for deposition processes include hydrogen, hydrazine, monoalkylhydrazine, dialkylhydrazine, and ammonia.

One type of structure in the metal precursor is illustrated in structure 1A below where the metal M has a valence of 2 having the formula:

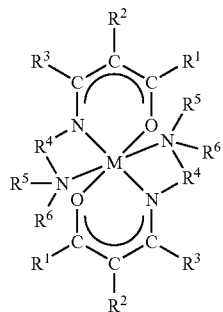

1A wherein M is selected from group 2, 8, 9, 10 metal atoms. In this precursor it is preferred that $R^1$ is a $C_{1-6}$ alkyl group, preferably a t-butyl or t-pentyl group when the metal is strontium and barium and $C_{1-6}$ when cobalt or nickel, $R^2$ and $R^3$ are methyl groups, $R^5$ and $R^6$ are individually lower $C_{1-3}$, preferably methyl groups and $R^4$ is a $C_{3-10}$ branched alkylene bridge having at least one chiral carbon atom, preferably a group containing 3 or 4 carbon atoms. Preferred metals are calcium, strontium, barium, iron, cobalt, and nickel.

Another type of structure within the first class of metal complexes containing tridentate β-ketoiminate ligands is illustrated in structure 2A below where the metal M has a valence of 3 having the formula:

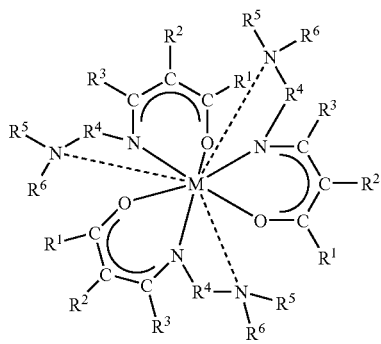

2A wherein M is selected from group 3 metal atoms. In this precursor it is preferred that $R^1$ is a $C_{4-6}$ alkyl group, preferably a t-butyl and t-pentyl group, $R^2$ and $R^3$ are methyl groups, $R^5$ and $R^6$ are individually lower $C_{1-3}$ alkyl, preferably methyl groups, and $R^4$ is a $C_{3-10}$ branched alkylene bridge having at least one chiral carbon atom, preferably a group containing 3 or 4 carbon atoms. Preferred metals are scandium, yttrium, and lanthanum.

The second class of metal-containing precursors are comprised of tridentate β-ketoiminate ligands as shown in formula B:

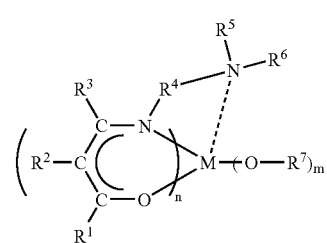

B wherein M is a Group 4 or 5 metal such as titanium, zirconium, or hafnium. As shown the complex consists of at least one alkoxy ligand and a tridentate β-ketoiminato ligand having at least one amino organo imino functionality. The preferred $R^{1-6}$ groups are the same as in formula A. The preferred $R^7$ group is a linear or branched alkyl, e.g., isopropyl, butyl, sec-butyl, and tert-butyl, m and n are at least 1 and the sum of m+n is equal to the valence of the metal.

The tridentate β-ketoiminate ligands can be prepared by well known procedure such as the Claisen condensation of a bulky ketone and an ethyl ester in presence of a strong base such as sodium amide or hydride, followed by another known procedure such as Schiff base condensation reaction with alkylaminoalkylamine. The ligands can be purified via vacuum distillation for a liquid or crystallization for solid.

As a preferred method for the formation of high yield and thermal stable tridentate ligands, it is preferred to choose a bulky $R^1$ group, e.g., $C_{4-6}$ alkyl groups without hydrogen attached to the carbon connected to the ketone functionality, most preferred $R^1$ group is tert-butyl or tert-pentyl. The $R^1$ group prevents side reactions occurring in the following Schiff condensation and later protecting the metal centers from inter-molecular interaction. There is a competing issue and that is that the $R^{1-7}$ groups in the tridentate ligands should be as small as possible in order to decrease the molecular weight of the resulting metal-containing complexes and allow the achievement of complexes having a high vapor pressure. The preferred $R^4$ is a branched alkylene bridge having at least one chiral carbon atom, most preferably a group containing 3 or 4 carbon atoms in order to make the resulting complexes more stable via forming a five- or six-membered coordinating ring to the metal center. The chiral center in the ligand plays a crucible in terms of lowering down the melting point as well as increasing the thermal stability.

The metal-containing complexes can then be prepared via the reaction of the resulting tridentate ligands with pure metal, metal amide, metal hydride, and metal alkoxide. The metal-containing complexes can also be prepared via reacting the tridentate ligand with alkyl lithium or potassium hydride to provide the lithium or potassium salt of the ligand, then followed by reaction with metal halide, $MX_n$ (X=Cl, Br, I; n=2, 3). The group 4 and 5 mixed ligand complexes can be made via changing the ratio of metal alkoxide to the tridentate ligands.

These metal-containing complexes with tridentate β-ketoiminate ligands can be employed as potential precursors to make thin metal or metal oxide films via either the chemical vapor deposition (CVD) or atomic layer deposition (ALD) method at temperatures less than 500° C. The CVD process can be carried out with or without reducing or oxidizing agents whereas an ALD process usually involves the employment of another reactant such as a reducing agent or oxidizing agent.

For multi-component metal oxide, these complexes can be premixed if they have the same tridentate β-ketoiminate ligands. These metal-containing complexes with tridentate β-ketoiminate ligands can be delivered in vapor phase into a CVD or ALD reactor via well-known bubbling or vapor draw techniques. A direct liquid delivery method can also be employed by dissolving the complexes in a suitable solvent or a solvent mixture to prepare a solution with a molar concentration from 0.001 to 2 M depending the solvent or mixed-solvents employed.

The solvent employed in solubilizing the precursor for use in a deposition process may comprise any compatible solvent in a mixture including aliphatic hydrocarbons, aromatic hydrocarbons, ethers, esters, nitrites, and alcohols. The solvent component of the solution preferably comprises a solvent selected from the group consisting of glyme solvents having from 1 to 20 ethoxy —$(C_2H_4O)$— repeat units; $C_2$-$C_{12}$ alkanols, organic ethers selected from the group consisting of dialkyl ethers comprising $C_1$-$C_6$ alkyl moieties, $C_4$-$C_8$ cyclic ethers; $C_{12}$-$C_{60}$ crown $O_4$-$O_{20}$ ethers wherein the prefixed $C_i$ range is the number i of carbon atoms in the ether compound and the suffixed $O_i$ range is the number i of oxygen atoms in the ether compound; $C_6$-$C_{12}$ aliphatic hydrocarbons; $C_6$-$C_{18}$ aromatic hydrocarbons; organic esters; organic amines, polyamines and organic amides.

Another class of solvents that offers advantages is the organic amide class of the form RCONR'R" wherein R and R' are alkyl having from 1-10 carbon atoms and they can be connected to form a cyclic group $(CH_2)_n$, wherein n is from 4-6, preferably 5, and R" is selected from alkyl having from 1 to 4 carbon atoms and cycloalkyl. N-methyl- or N-ethyl- or N-cyclohexyl-2-pyrrolidinones, N,N-Diethylacetamide, and N,N-Diethylformamide are examples.

The following example illustrates the preparation of the metal-containing complexes with tridentate β-ketoiminate ligands as well as their use as precursors in metal-containing film deposition processes.

EXAMPLE 1

Synthesis of 2,2-dimethyl-5-(1-dimethylamino-2-propylimino)-3-hexanone

To a solution of 13.55 g (95.29 mmol) 2,2-dimethyl-3,5-hexanedione in 150 mL of THF containing with 20 g (140.81 mmol) of sodium sulfate was added 11.68 g (114.34 mmol) of 1-dimethylamino-2-propylamine. Reaction mixture was heated to 65° C. for 72 hours. After completion, THF was evaporated under vacuum and excess 1-dimethylamino-2-propylamine was distilled by heating the mixture at 80° C. under 140 mTorr vacuum for one hour. Residual oil was subjected to vacuum transfer heating at 110° C. under 100 mTorr vacuum. 18.75 g of a lime-green yellow oil was obtained and GC analysis indicates 99% purity. The yield was 87%.

$^1$H NMR (500 MHz, $C_6D_6$): δ=11.51 (s, 1H), 5.20 (s, 1H), 3.24 (m, 1H), 1.91 (m, 2H), 1.91 (s, 6H), 1.60 (s, 3H), 1.32 (s, 9H), 0.94 (d, 3H).

EXAMPLE 2

Synthesis of bis(2,2-dimethyl-5-(1-dimethylamino-2-propylimino)-3-hexanonato-N,O,N')strontium To a solution of 1 g (1.81 mmol) $Sr(N(SiMe_3)_2)_2)·(THF)_2$ in 10 mL THF was added 0.82 g (3.62 mmol) 2,2-dimethyl-5-(1-dimethylamino-2-propylimino)-3-hexanone in 10 mL of THF dropwise at room temperature. Stirred for 16 hours. THF was evaporated off under vacuum to provide an off-white solid that was taken up as a solution in hexanes. Evaporated off hexanes and dry solid was recrystallized in pentane at room temperature. 0.48 g of clear needle-like crystals were obtained (50% yield based on Sr).

Elemental analysis: calculated for C26H50N4O2Sr: C, 58.01; N, 10.40; H, 9.36. Found: C, 56.07; N, 10.10; H, 8.86. $^1$H NMR (500 MHz, $C_6D_6$): δ=5.12 (s, 1H), 3.42 (m, 1H), 3.32 (t, 1H), 1.96 (b, 2H), 1.83 (s, 6H), 1.72 (b, 2H), 1.41 (s, 9H), 0.94 (d, 3H).

A colorless crystal was structurally characterized by single crystal analysis. The structure shows strontium coordinated with two oxygen and four nitrogen atoms from the two tridentate ketominate ligands in a distorted octahedral environment. This is illustrated in FIG. 1 in which there are ethylene bridges between the two nitrogen atoms of the imino functionality for $R^4$ shown as C4, C5 and C18, C17. C4 and C17 are chiral atoms as they are connected to four different substituents, i.e. H, N1, C11, C5 for C4 and H, N3, C18, C24 for C17.

Figure 2:
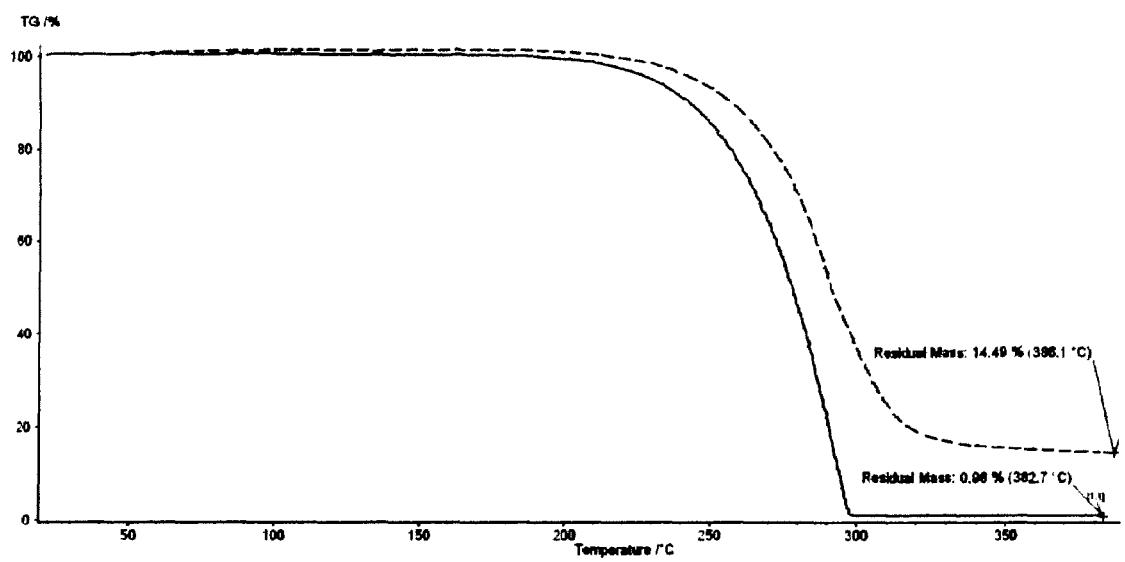
FIG. 2 is thermogravimetric analysis (TGA) diagrams of bis(2,2-dimethyl-5-(1-dimethylamino-2-propylimino)-3-hexanonato-N,O,N')strontium (solid line) vs bis(2,2-dimethyl-5-(dimethylaminoethyl-imino)-3-hexanonato-N,O,N') strontium (dashed line), indicating the new Sr complex with a chiral center (solid line) is much more stable than that without chiral center between the two nitrogen atoms (dashed line), thus leaving almost no residue.

FIG. 2 shows a TGA of the compound of Example 2 having ethylene bridges with chiral centers between the two nitrogen atoms of the imino functionality for $R^4$; in contrast to the analogous compound where $R^4$ is an ethylene bridge without chiral centers. The compound of Example 2 is shown by the solid line, while the analogous compound where $R^4$ is an ethylene bridge is shown by the dotted line. A larger residue in a TGA analysis typifies compounds having less stability. Thus, the compound of Example 2 has less than 1% residue whereas the analogous compound without chiral centers over 14% residue, indicating a substantial enhancement in thermal stability necessary when used as a precursor to deposit metal-containing films in a deposition in semiconductor fabrication.

EXAMPLE 3

Synthesis of bis(2,2-dimethyl-5-(1-dimethylamino-2-propylimino)-3-hexanonato-N,O,N')nickel To a solution of 3.49 g (15.43 mmol) 2,2-dimethyl-5-(1-dimethylamino-2-propylimino)-3-hexanone in 10 mL of hexanes at −78° C. in dry ice/acetone bath was added 6.17 mL (15.43 mmol) of 2.5M n-butyl lithium in hexanes dropwise. Warmed solution to room temperature and left to stir for one hour. Hexanes was evaporated from solution under vacuum and a residual sticky yellow oil was obtained. 20 mL of THF was added to the residual and this solution was added to 1.00 g (7.72 mmol) $NiCl_2$ in 10 mL of THF at room temperature. Stirred for 96 hours under argon heating at 60° C. Evaporated off THF under vacuum and residual dark green solid was taken up in hexanes, heated, and filtered. Evaporated hexanes under vacuum and obtained 3.5 g of a sticky dark green solid that was sublimed at 100° C. under 65 mTorr of vacuum for 48 hours yielding 2.8 g of a green solid (70% yield). Sublimed material was recrystallized by slow evaporation of pentane at room temperature.

Elemental Analysis: calculated for C26H50N4NiO2: C, 61.30; H, 9.89; N, 11.00. Found: C, 59.18; H, 9.09; N, 10.84.

Figure 3:
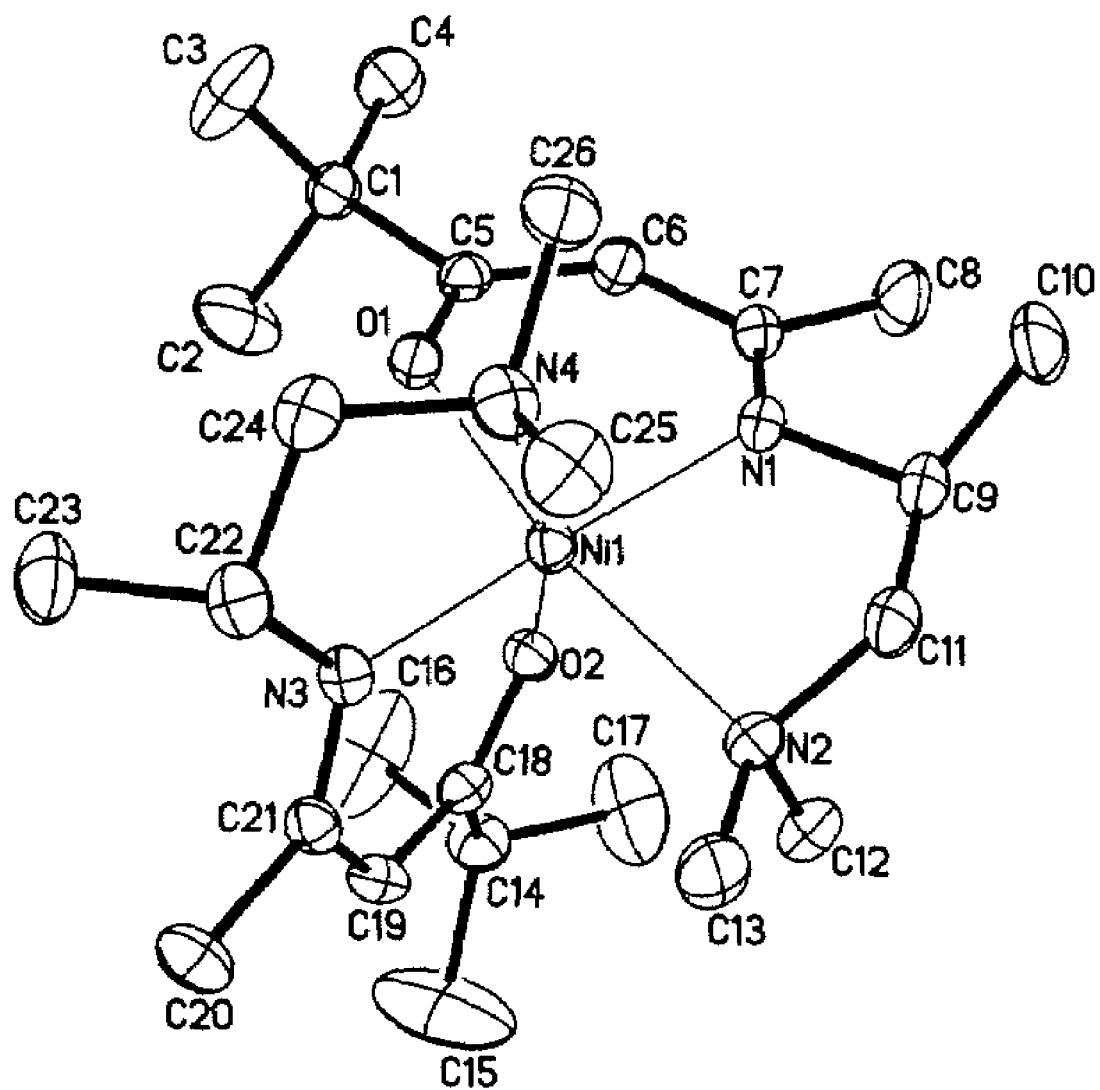
FIG. 3 is a drawing representing the crystal structure of bis(2,2-dimethyl-5-(1-dimethylamino-2-propylimino)-3-hexanonato-N,O,N')nickel.

A dark green crystal was structurally characterized by single crystal analysis. The structure shows nickel coordinated with two oxygen and four nitrogen atoms from the two tridentate ketominate ligands in a distorted octahedral environment. This is illustrated in FIG. 3 in which there are ethylene bridges between the two nitrogen atoms of the imino functionality for $R^4$ shown as C9, C11 and C22, C23. C9 and C22 are chiral atoms as they are connected to four different substituents, i.e. H, N1, C10, C11 for C9 and H, N3, C23, C24 for C22.

Figure 4:
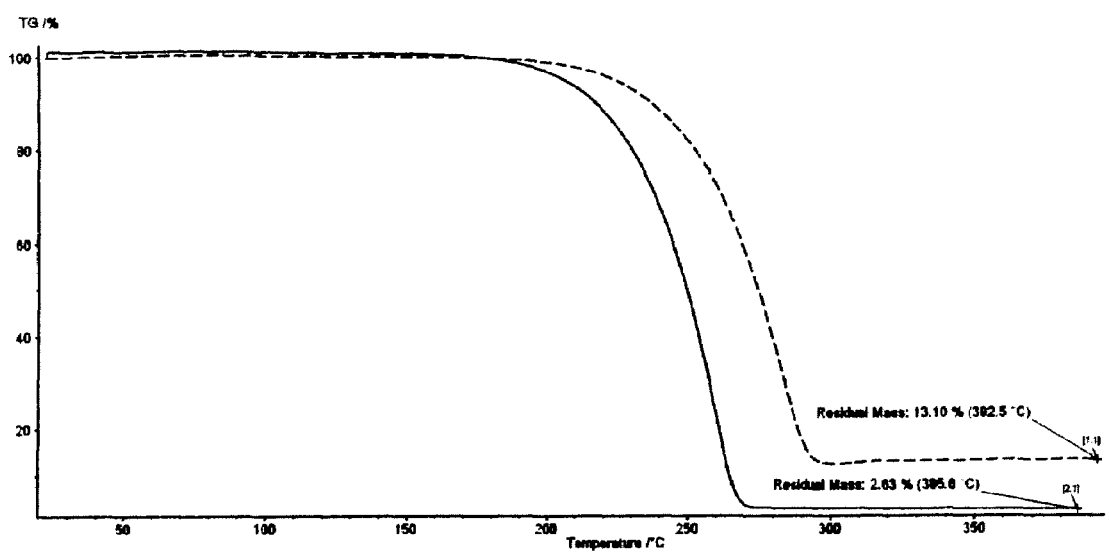
FIG. 4 is thermogravimetric analysis (TGA) diagrams of bis(2,2-dimethyl-5-(1-dimethylamino-2-propylimino)-3-hexanonato-N,O,N')nickel (solid line) vs bis(2,2-dimethyl-5-(dimethylaminoethyl-imino)-3-hexanonato-N,O,N')nickel (dashed line), indicating the new Ni complex with a chiral center (solid line) is much more stable than that without chiral center between the two nitrogen atoms (dashed line), thus leaving less than 2% residue.

FIG. 4 shows a TGA of the compound of Example 3 having ethylene bridges with chiral centers between the two nitrogen atoms of the imino functionality for R⁴; in contrast to the analogous compound where R⁴ is an ethylene bridge without chiral centers. The compound of Example 3 is shown by the solid line, while the analogous compound where R⁴ is an ethylene bridge without chiral centers is shown by the dotted line. A larger residue in a TGA analysis typifies compounds having less stability. Thus, the compound of Example 3 has approximately less than 3% residue whereas the analogous compound over 13% residue, indicating a substantial enhancement in thermal stability necessary when used as a precursor to deposit metal-containing films in a deposition in semiconductor fabrication.

EXAMPLE 4

Synthesis of Ti(O-$^i$Pr)$_3$(2,2-dimethyl-5-(1-dimethylamino-2-propylimino)-3-hexanonato To a solution of 1 g (3.52 mmol) titanium(IV)isopropoxide in 15 mL of hexanes was added 0.80 g (3.52 mmol) 2,2-dimethyl-5-(1-dimethylamino-2-propylimino)-3-hexanone and reaction mixture was heated to 60° C. for 16 hours. Evaporated off volatiles under vacuum and obtained 1.59 g of a crude grainy oil.

$^1$H NMR (500 MHz, C$_6$D$_6$): δ=5.32 (s, 1H), 5.10 (b, 3H), 3.20 (m, 1H), 2.40 (b, 2H), 2.40 (b, 6H), 1.64 (s, 3H), 1.39 (d, 18H), 1.36 (s, 9H), 1.27 (b, 3H).

Figure 5:
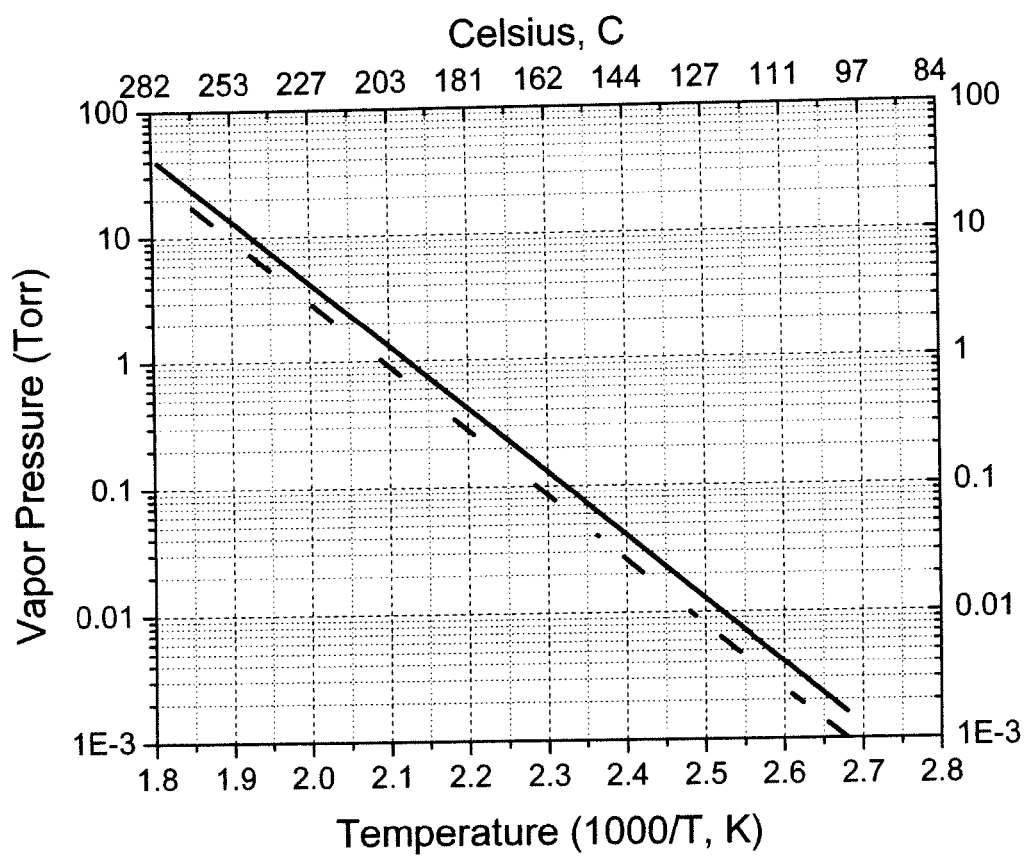
FIG. 5 is comparison of vapor pressure of bis(2,2-dimethyl-5-(1-dimethylamino-2-propylimino)-3-hexanonato-N,O,N')strontium (solid line) vs bis(2,2-dimethyl-5-(dimethylaminoethyl-imino)-3-hexanonato-N,O,N')strontium (dashed line), indicating the new Sr complex with a chiral center (solid line) is more volatile than that without chiral center between the two nitrogen atoms (dashed line) although the molecular weight of bis(2,2-dimethyl-5-(dimethylaminoethyl-imino)-3-hexanonato-N,O,N')strontium is smaller than bis(2,2-dimethyl-5-(1-dimethylamino-2-propylimino)-3-hexanonato-N,O,N')strontium.

One of the crucial requirements for precursors employed for chemical vapor deposition and atomic layer deposition is that the precursor has to be stable during the delivery temperature, generally ranging from 40 to 150° C. The thermogravimetric analysis (TGA) is widely used as a tool to screen compounds. The measurements of the compounds of the present invention were carried out in open aluminum crucibles with sample sizes of 10 to 20 mg inside a dry box. The temperature ramp rate is usually 10 C.°/min. As the temperature increases, the compound starts to undergo either vaporization or decomposition or both. Pure vaporization leads to almost no residue, whereas vaporization plus decomposition results in certain degree of residue. Generally speaking, less residue in a TGA diagram suggests the compound is more thermally stable, thus more suitable to be a precursor for fabricating thin films. As shown in FIGS. 2 and 4, the compounds revealed in this invention have much less than residues than those prior analogues, suggesting they are more thermally stable and have a better capability to be employed as precursors. On the other hand, introduction of chiral centers is one approach to increase the thermal stability, as well as to lower the melting point of resulting metal compounds. A molecule is chiral if it cannot be superimposed on its mirror image, the two mirror images of such a molecule are referred to as enantiomers. If a carbon atom has four different substituents connected to it, it is chiral. For compounds in Example 2 and 3, there are two chiral carbon atoms, implying there are three enantiomers co-existing in the solid state, which scramble around, weakening the intermolecular interaction, thus increasing the volatility, as shown in FIG. 5, although bis(2,2-dimethyl-5-(dimethylaminoethyl-imino)-3-hexanonato-N,O,N')strontium is smaller than bis(2,2-dimethyl-5-(1-dimethylamino-2-propylimino)-3-hexanonato-N, O,N')strontium, and, in theory, bis(2,2-dimethyl-5-(1-dimethylamino-2-propylimino)-3-hexanonato-N,O,N') strontium should be less volatile than bis(2,2-dimethyl-5-(dimethylaminoethyl-imino)-3-hexanonato-N,O,N') strontium.

The invention claimed is:

1. A metal containing complex represented by the structures selected from the group consisting of:

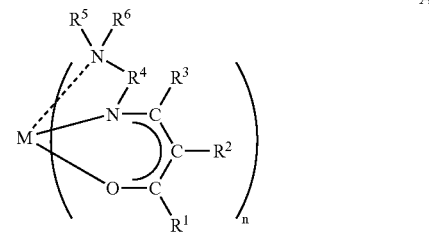

A wherein M is a metal group having a valence of from 2 to 5 wherein R¹ is selected from the group consisting of alkyl, fluoroalkyl, cycloaliphatic, and aryl, having from 1 to 10 carbon atoms; R² is selected from the group consisting of hydrogen, alkyl, alkoxy, cycloaliphatic, and aryl; R³ is selected from the group consisting of alkyl, fluoroalkyl, cycloaliphatic, and aryl; R⁴ is a C3-10 branched alkylene bridge having at least one chiral carbon atom; R⁵⁻⁶ are individually selected from the group consisting of alkyl, fluoroalkyl, cycloaliphatic, aryl, and heterocyclic containing either oxygen, or nitrogen atoms; n is an integer equal to the valence of the metal M;

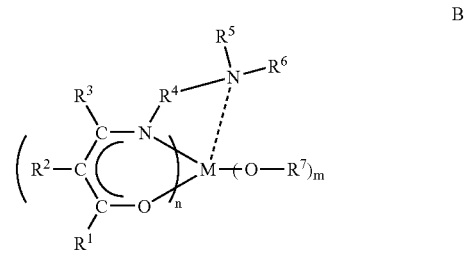

B wherein M is a metal ion selected from Group 4 and 5 metals; wherein R¹ is selected from the group consisting of alkyl, fluoroalkyl, cycloaliphatic, and aryl, having from 1 to 10 carbon atoms; R² is selected from the group consisting of hydrogen, alkyl, alkoxy, cycloaliphatic, and aryl; R³ is selected from the group consisting of alkyl, fluoroalkyl, cycloaliphatic, and aryl; R⁴ is a C3-10 branched alkylene bridge having at least one chiral carbon atom; R⁵⁻⁶ are individually selected from the group consisting of alkyl, fluoroalkyl, cycloaliphatic, aryl, or heterocyclic containing an oxygen, or nitrogen atom; R⁷ is selected from the group consisting of alkyl, fluoroalkyl, cycloaliphatic, and aryl; and wherein m and n are at least 1 and the sum of m plus n is equal to the valence of the metal M.

2. The metal containing complex of claim 1 structure A wherein M is selected from the group consisting of calcium, strontium, barium, scandium, yttrium, lanthanum, titanium, zirconium, vanadium, tungsten, manganese, cobalt, iron, nickel, ruthenium, zinc, copper, palladium, platinum, iridium, rhenium, and osmium.

3. The metal containing complex of claim 2 wherein R¹ is selected from the group from t-butyl and t-pentyl, R² and R³ are individually selected from the group consisting of methyl and ethyl, $R^4$ is a $C_3$ alkylene bridge with a chiral center, and $R^5$ and $R^6$ are individually selected from the group consisting of methyl and ethyl.

4. The metal containing complex of claim 3 wherein M is strontium, $R^1$ is t-butyl, $R^2$ and $R^3$ are methyl, $R^4$ is a $C_3$ alkylene bridge with a chiral center and $R^5$ and $R^6$ are selected from the group consisting of methyl and ethyl.

5. The metal containing complex of claim 1 represented by the structure B:
   wherein M is selected from the group consisting of titanium, zirconium, hafnium, vanadium, niobium, and tantalum.

6. The metal containing complex of claim 5 wherein $R^1$ is selected from the group consisting of $C_{1-5}$ alkyl, $R^2$ and $R^3$ are individually selected from the group consisting of methyl and ethyl, $R^4$ is a $C_{3-4}$ alkylene bridge with at least one chiral centers, $R^5$ and $R^6$ are individually selected from the group consisting of methyl and ethyl, and $R^7$ is selected the group consisting of methyl, ethyl, propyl, iso-propyl, n-butyl, sec-butyl, and tert-butyl.

7. The metal containing complex of claim 5 wherein M is Ti, $R^1$ is methyl, $R^2$ and $R^3$ are methyl, $R^4$ is a $C_3$ alkylene bridge with one chiral center and $R^5$ and $R^6$ methyl.

8. The metal containing complex of claim 5 wherein M is Hf, $R^1$ is methyl, $R^2$ and $R^3$ are methyl, $R^4$ is a $C_3$ alkylene bridge with one chiral center and $R^5$ and $R^6$ methyl.

9. The metal containing complex of claim 5 wherein M is Zr, $R^1$ is methyl, $R^2$ and $R^3$ are methyl, $R^4$ is a $C_3$ alkylene bridge with one chiral center and $R^5$ and $R^6$ are methyl.

10. The metal containing complex of claim 5 wherein M is Ti, $R^1$ is t-butyl, $R^2$ and $R^3$ are methyl, $R^4$ is a $C_3$ alkylene bridge and $R^5$ and $R^6$ are methyl.

11. The metal containing complex of claim 5 wherein M is Hf, $R^1$ is t-butyl, $R^2$ and $R^3$ are methyl, $R^4$ is a $C_3$ alkylene bridge with one chiral center and $R^5$ and $R^6$ are methyl.

12. The metal containing complex of claim 5 wherein M is Zr, $R^1$ is t-butyl, $R^2$ and $R^3$ are methyl, $R^4$ is a $C_3$ alkylene bridge with one chiral center and $R^5$ and $R^6$ are methyl.

13. The metal containing complex of claim 1 dissolved in a solvent selected from the group consisting of glyme solvents having from 1 to 20 ethoxy —$(C_2H_4O)$—repeat units; $C_2$-$C_{12}$ alkanols, organic ethers selected from the group consisting of dialkyl ethers comprising $C_1$-$C_6$ alkyl moieties, $C_4$-$C_8$ cyclic ethers; $C_{12}$-$C_{60}$ crown $O_4$-$O_{20}$ ethers wherein the prefixed $C_i$ range is the number i of carbon atoms in the ether compound and the suffixed $O_i$ range is the number i of oxygen atoms in the ether compound; $C_6$-$C_{12}$ aliphatic hydrocarbons; $C_6$-$C_{18}$ aromatic hydrocarbons; organic esters; organic amines; and polyamines and organic amides.

14. The metal containing complex of claim 13 wherein the solvent is an organic amide selected from the group consisting N-methyl-2-pyrrolidinone, N-ethyl-2- pyrrolidinone, N-cyclohexyl-2-pyrrolidinone, N,N-Diethylacetamide, and N,N-Diethylformamide.

15. A vapor deposition process for forming a conformal metal oxide thin film on a substrate wherein a precursor source and an oxygen containing agent are introduced to a deposition chamber and a metal oxide film deposited on a substrate, the improvement which comprises using as said precursor source a metal containing complex represented by the structures selected from the group consisting of:

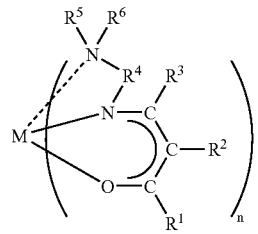

A wherein M is a metal group having a valence of from 2 to 5 wherein $R^1$ is selected from the group consisting of alkyl, fluoroalkyl, cycloaliphatic, and aryl, having from 1 to 10 carbon atoms; $R^2$ is selected from the group consisting of hydrogen, alkyl, alkoxy, cycloaliphatic, and aryl; $R^3$ is selected from the group consisting of alkyl, fluoroalkyl, cycloaliphatic, and aryl; $R^4$ is a C3-10 branched alkylene bridge having at least one chiral carbon atom; $R^{5-6}$ are individually selected from the group consisting of alkyl, fluoroalkyl, cycloaliphatic, aryl, and heterocyclic containing either oxygen, or nitrogen atoms; n is an integer equal to the valence of the metal M;

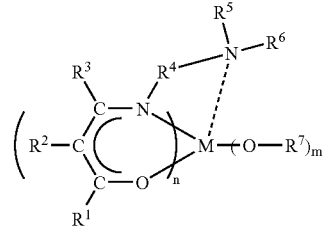

B wherein M is a metal ion selected from Group 4 and 5 metals; wherein $R^1$ is selected from the group consisting of alkyl, fluoroalkyl, cycloaliphatic, and aryl, having from 1 to 10 carbon atoms; $R^2$ is selected from the group consisting of hydrogen, alkyl, alkoxy, cycloaliphatic, and aryl; $R^3$ is selected from the group consisting of alkyl, fluoroalkyl, cycloaliphatic, and aryl; $R^4$ is a C3-10 branched alkylene bridge having at least one chiral carbon atom; $R^{5-6}$ are individually selected from the group consisting of alkyl, fluoroalkyl, cycloaliphatic, aryl, or heterocyclic containing an oxygen, or nitrogen atom; $R^7$ is selected from the group consisting of alkyl, fluoroalkyl, cycloaliphatic, and aryl; and wherein m and n are at least 1 and the sum of m plus n is equal to the valence of the metal M.

16. The vapor deposition process of claim 15 wherein the vapor deposition process is selected from the group consisting of chemical vapor deposition, plasma enhanced chemical vapor deposition, atomic layer deposition, and plasma enhanced atomic layer deposition.

17. The vapor deposition process of claim 15 wherein the oxygen containing agent is selected from the group consisting of water, $O_2$, $H_2O_2$, ozone and mixtures thereof.

18. A vapor deposition process for forming a conformal metal thin film on a substrate wherein a precursor source and a reducing agent are introduced to a deposition chamber and a metal film deposited on a substrate, the improvement which comprises using as said precursor source a metal containing complex represented by the structures selected from the group consisting of:

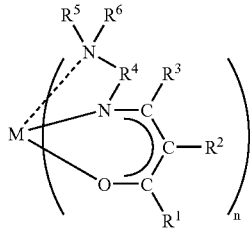

A wherein M is a metal group having a valence of from 2 to 5 wherein $R^1$ is selected from the group consisting of alkyl, fluoroalkyl, cycloaliphatic, and aryl, having from 1 to 10 carbon atoms; $R^2$ is selected from the group consisting of hydrogen, alkyl, alkoxy, cycloaliphatic, and aryl; $R^3$ is selected from the group consisting of alkyl, fluoroalkyl, cycloaliphatic, and aryl; $R^4$ is a C3-10 branched alkylene bridge having at least one chiral carbon atom; $R^{5-6}$ are individually selected from the group consisting of alkyl, fluoroalkyl, cycloaliphatic, aryl, and heterocyclic containing either oxygen, or nitrogen atoms; n is an integer equal to the valence of the metal M;

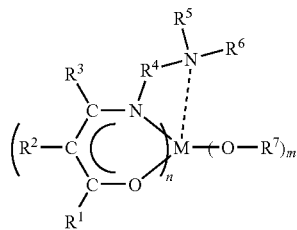

B wherein M is a metal ion selected from Group 4 and 5 metals; wherein $R^1$ is selected from the group consisting of alkyl, fluoroalkyl, cycloaliphatic, and aryl, having from 1 to 10 carbon atoms; $R^2$ is selected from the group consisting of hydrogen, alkyl, alkoxy, cycloaliphatic, and aryl; $R^3$ is selected from the group consisting of alkyl, fluoroalkyl, cycloaliphatic, and aryl; $R^4$ is a C3-10 branched alkylene bridge having at least one chiral carbon atom; $R^{5-6}$ are individually selected from the group consisting of alkyl, fluoroalkyl, cycloaliphatic, aryl, or heterocyclic containing an oxygen, or nitrogen atom; $R^7$ is selected from the group consisting of alkyl, fluoroalkyl, cycloaliphatic, and aryl; and wherein m and n are at least 1 and the sum of m plus n is equal to the valence of the metal M.

19. The the vapor deposition process of claim 18 wherein the reducing agent is selected from the group consisting of hydrogen, hydrazine, monoalkylhydrazine, dialkylhydrazine, ammonia, and mixtures thereof.

20. A vapor deposition process for forming a conformal metal oxide thin film on a substrate wherein a solution of precursor source and an oxygen containing agent are introduced to a deposition chamber and a metal oxide film deposited on a substrate, the improvement which comprises using a solution of comprised of the metal containing complex of claim 15 dissolved in a solvent selected from the group consisting of glyme solvents having from 1 to 20 ethoxy —$(C_2H_4O)$—repeat units; $C_2$-$C_{12}$ alkanols, organic ethers selected from the group consisting of dialkyl ethers comprising $C_1$-$C_6$ alkyl moieties, $C_4$-$C_8$ cyclic ethers; $C_{12}$-$C_{60}$ crown $O_4$-$O_{20}$ ethers wherein the prefixed $C_i$ range is the number i of carbon atoms in the ether compound and the suffixed $O_i$ range is the number i of oxygen atoms in the ether compound; $C_6$-$C_{12}$ aliphatic hydrocarbons; $C_6$-$C_{18}$ aromatic hydrocarbons; organic esters; organic amines; and polyamines and organic amides.

21. A vapor deposition process for forming a conformal metal thin film on a substrate wherein a solution of a precursor source and a reducing agent are introduced to a deposition chamber and a metal film deposited on a substrate, the improvement which comprises using a solution comprised of the metal containing complex of claim 18 dissolved in a solvent selected from the group consisting of glyme solvents having from 1 to 20 ethoxy —$(C_2H_4O)$— repeat units; $C_2$-$C_{12}$ alkanols, organic ethers selected from the group consisting of dialkyl ethers comprising $C_1$-$C_6$ alkyl moieties, $C_4$-$C_8$ cyclic ethers; $C_{12}$-$C_{60}$ crown $O_4$-$O_{20}$ ethers wherein the prefixed $C_i$ range is the number i of carbon atoms in the ether compound and the suffixed $O_i$ range is the number i of oxygen atoms in the ether compound; $C_6$-$C_{12}$ aliphatic hydrocarbons; $C_6$-$C_{18}$ aromatic hydrocarbons; organic esters; organic amines; and polyamines and organic amides.

* * * * *